United States Patent [19]

Cosman

[11] Patent Number: 4,653,508
[45] Date of Patent: Mar. 31, 1987

[54] PRESSURE-BALANCED TELEMETRIC PRESSURE SENSING SYSTEM AND METHOD THEREFORE

[76] Inventor: Eric R. Cosman, 872 Concord Ave., Belmont, Mass. 02178

[21] Appl. No.: 227,900

[22] Filed: Jan. 23, 1981

Related U.S. Application Data

[63] Continuation of Ser. No. 945,364, Sep. 25, 1978, abandoned, which is a continuation of Ser. No. 697,951, Jun. 21, 1976, abandoned.

[51] Int. Cl.$^4$ ............................................. A61B 5/00
[52] U.S. Cl. ....................................... 128/748; 73/716
[58] Field of Search ........... 128/748; 73/701, 715–722

[56] References Cited

U.S. PATENT DOCUMENTS

| | | | |
|---|---|---|---|
| 4,022,190 | 5/1977 | Meyer | 128/748 |
| 4,027,661 | 6/1977 | Lyon et al. | 128/748 |
| 4,124,023 | 11/1978 | Fleischmann et al. | 128/748 X |

Primary Examiner—Kyle L. Howell
Assistant Examiner—Francis J. Jaworski
Attorney, Agent, or Firm—Richard J. Birch

[57] ABSTRACT

A differential pressure sensing device is fully implanted in the body of a patient to monitor internal pressure such as intracranial pressure. A movable element in the sensor communicates on one side with the internal pressure to be measured and on the other side with an external pressure which is applied by an external pressurizer-control system and which is communicated to the sensor through the intact skin. An imbalance of the two opposing pressures causes a displacement of the movable element which changes a physical characteristic of the sensor, such as the resonant frequency of a tuned L-C circuit. This change is detected outside the body by an external detection system, such as a frequency swept radio frequency oscillator. The external pressure is varied until the external detector senses that the pressures are balanced on the movable element, at which point the external pressure equals the internal pressure, and the former is measured and read out.

110 Claims, 14 Drawing Figures

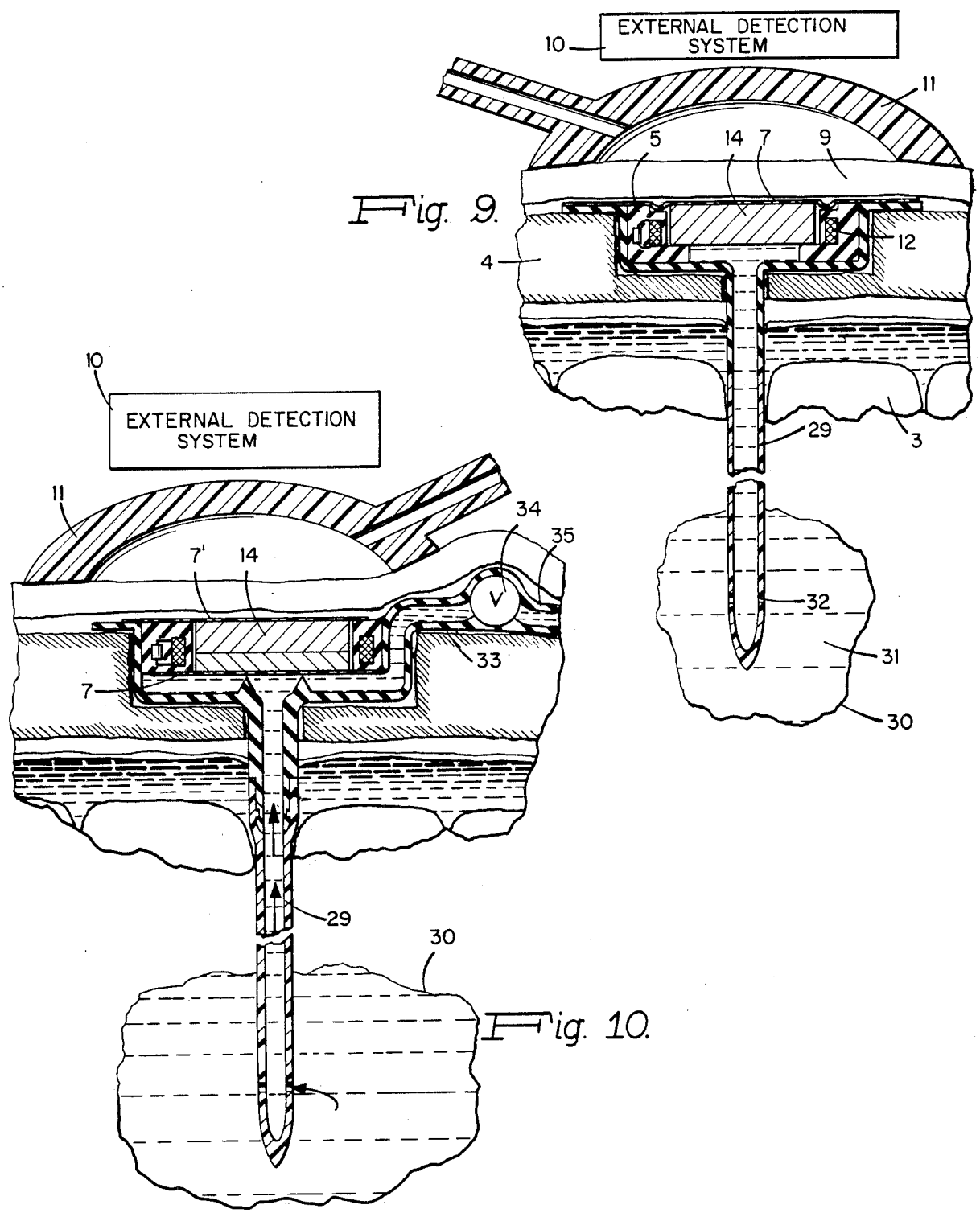

PRESSURE-BALANCED TELEMETRIC PRESSURE SENSING SYSTEM AND METHOD THEREFORE

This is a continuation of application Ser. No. 945,364, filed Sept. 25, 1978 and now abandoned, which is a continuation of Ser. No. 697,951 filed June 21, 1976, and now abandoned.

BACKGROUND OF THE INVENTION

The invention relates to the precision measurement and monitoring of pressures in a confined region and particularly in a living body, such as intracranial pressure in the head, by means of a long-term totally implanted pressure sensor which undergoes a conformational change with pressure and which is coupled through the skin by electromagnetic, acoustic, or mechanical transmission to an external device which detects that change and interprets the pressure. The invention refers additionally to a device which is automatically barometric compensated, has immediate zero point reference check, can be made passive, and is insensitive to barometric or temperature changes.

At the present time there is no such wireless device available for general clinical or research purposes. The uses for such a device in neurosurgery would be immediate in the management of intracranial hypertension, monitoring of intracranial pressure in all cases of intracranial neurosurgery and head trauma, long-term diagnostics for evidence of tumor recurrence, and management of hydrocephalus.

All devices previously proposed have significant shortcomings which make them impractical for widespread, safe, accurate, reliable, and longterm use as intracranial pressure monitors. Most designs involve a tube or wire connection through the skin to an external device, and since this greatly increases the chance of infection and electrical shock to the patient and reduces the patient's mobility, they are hazardous and impractical. Of the devices which are wireless and fully implanted, they usually involve a sealed inner volume containing a fixed amount of gas, this being housed in a flexible container which deflects under pressure. The major problems with this design aspect are the following: liquids and gases will inevitably diffuse through the membranes and walls of the container causing steady drift of the zero-point reading, and causing an unpredictable error in the device's calibration; changes in barometric pressure will cause significant variations in the body pressure relative to the fixed volume pressure and thus the device's pressure readout must be corrected for barometric pressure changes in the external detection system; a trapped volume of significant size could make it dangerous for a patient to experience atmospheric pressure change, such as those found in air travel, for fear of rupturing the device; and temperature changes in the patient will cause changes in the trapped volume and resultant errors in the pressure reading. Previous totally implanted designs provide no means to check their zero-pressure calibration after implantation and thus no means to determine diffusion or temperature drifts in the readings nor any check of the proper function of the device, which is essential for long and short-term implantation. Most previous designs are of complex construction, involve high tolerance parts and assembly, and are not amenable to calibration standardization; all of which make them expensive, inaccurate, and unsuitable for simple and general application.

Accordingly, some of the principal objects of the present invention are the following:

(1) To provide a pressure detector which can be implanted for an indefinite period under a fully intact skin with no wire or tube connections to the exterior so as to reduce infection and electrical shock hazard, and to read pressures in inaccessible spaces in the body, such as intracranial pressure, with an accuracy of 5 to 10% or better.

(2) To eliminate or make insignificant all inaccuracies, and dependencies on a trapped volume of gas or fluid in the device, to make the pressure readings insensitive to drifts from membrane permeability, barometric change and temperature variation, and to eliminate the hazard of rupturing the device during air travel.

(3) To provide automatic barometric compensation as a built-in feature of the implanted device.

(4) To provide a means of easily and instantly checking the zero-pressure calibration of the device.

(5) To provide a sufficiently fast dynamic response to enable observation of variations in the body pressure due to heart rate, respiration, and any other physiological changes.

(6) To allow a simple calibration standardization of the implant.

(7) To allow the implanted device to be of simple, passive, compact, and low cost construction so as to be implanted permanently and to function properly for indefinitely long periods.

(8) To make the system amenable to telemetry over long distances so as to monitor pressures in a freely moving patient.

SUMMARY OF THE INVENTION

The invention enables the precision measurement of pressure inside the living body without a break through the skin or wires or tubes through the skin and involves a novel differential pressure sensing device fully implanted in the body, an external detection system which can interrogate the implanted sensor in the body, an external pressurizing system which can control and measure pressure which is applied to the skin in the region of the implanted sensor, and a means of displaying and recording the pressure applied by the external pressurizing-control system. The principle of operation of the invention is the following: the fully implanted sensor, which is covered by a completely intact skin, contains a movable element which feels the internal bodily pressure to be measured on one side and an external pressure applied through the intact skin over the sensor by the pressurizing-control system on the other side, so that its equilibrium position corresponds to a balancing or equality of the two pressures. This equilibrium condition or balanced position of the movable element is detected with an external detection system by means of a electromagnetic, acoustic, radiation, mechanical, or other methods of coupling across the skin to the implanted sensor. The externally applied pressure on the skin, which corresponds to the internal body pressure when the balance condition is attained, can be measured with high precision and may be controlled manually or automatically and varied until the balanced condition is detected. The implanted sensor can have a built-in fiducial point corresponding to the pressure balanced position of the movable element which can be checked at any time by pressing manually on the skin covering the sensor, thereby bringing the movable element to the fiducial position and allowing the external detection system to be adjusted or "zeroed" relative to it. In operation, a deviation from this reference position caused by a difference in pressures across the implanted sensor is detected by the external detection system and an associated error signal can be used to increase or decrease the externally applied pressure so as to equalize the internal and external pressures. In this way the external pressurizing-control system can be made to track variations in the internal pressure to be measured.

A specific illustration of this invention will be given in which the implanted sensor contains a passive L-C tank circuit, the inductance, capacitance, or both of which are pressure dependent. The resonant frequency of this circuit is thus pressure dependent and is detected by the external detection system in order to determine if the system is or is not in the pressure balanced condition, which information may be used to provide an error signal to the external pressurizing-control system. The external detection system in this case is coupled electromagnetically to the implanted sensor and may embody a swept frequency, energy dip oscillator to detect the sensor's resonant frequency. Several other ways of implementing this invention concept will be cited. Several illustrative embodiments of the invention will be shown which have application in measuring and monitoring intracranial pressure.

The present invention has all of the novel and unique advantages of the wireless and tubeless pressure measuring device described in U.S. patent application Ser. No. 697-948, filed on June 21, 1976 by the present inventor and now abandoned and in addition has several other novel features and differences. Like the said other invention, the present invention makes use of pressure transmission through the fully intact skin and does not compress a trapped volume of gas in the sensor, and this eliminates problems of zero-point calibration drift, barometric compensation, and rupture hazard. However, the said other invention uses only atmospheric external pressure and relies further on a spring in the sensor to provide a calibrated displacement of a movable element in the sensor for a given internal pressure to be measured. In contrast, the present invention eliminates the spring force by applying an externally controlled pressure to the sensor across the skin and thus makes the pressure measurement at only one position corresponding to zero displacement of the movable element in the sensor; thus placing the burden of pressure calibration in the external equipment and eliminating inaccuracies due to surface tension effects at non-zero displacements. The method of the present invention has the resulting advantages of greater accuracy, range of pressure measurement, linearity, and simplicity of sensor construction.

DESCRIPTION OF THE DRAWINGS

Further objects, advantages, and aspects of the present invention can be gained from the following detailed description, illustrative drawings, and various embodiments and implementations. Illustrations will be given for measuring intracranial pressure although uses in other parts of the body are possible. In the following drawings similar reference characters represent similar parts.

FIG. 9 shows a pressure sensor similar to that of FIG. 2 with specific design variations and an attached catheter.

FIG. 10 shows a combination of the present invention with a catheter and a fluid shunt valve for control of hydrocephalus.

FIG. 13 illustrates a different version of the dual diaphragm, fluid motion coupling embodiment of the invention;

FIG. 14 illustrates still another version of the dual diaphragm, fluid motion coupling embodiment of the invention.

FIG. 1 illustrates the major elements of the implanted pressure sensor, used in this example as a monitor of epidural intracranial pressure if the dural membrane 1 is intact or of cerebrospinal fluid 2 pressure that surrounds the brain 3 if the dura 1 is cut. The sensor, which is inserted into a burrhole drilled in the skull 4 comprises a housing 5 which has a through opening in it in which moves a movable element 6. An inner flexible diaphragm 7 attached to the housing 5 communicates the intracranial pressure $P_{ICP}$ inside the skull to one side of the movable element 6 and an outer flexible diaphragm 7' communicates the external pressure $P_{EXT}$ in the region 8, which is transmitted across the intact scalp 9, to the other side of movable element 6. By this system a difference $\Delta P = P_{ICP} - P_{EXT}$ will cause a force imbalance on element 6, and for example if $\Delta P$ is positive that net force will cause the movable element and flexible diaphragms 7 and 7' to be displaced upward. If $P_{EXT}$ is then increased so as to balance the pressure $P_{ICP}$, i.e. $P_{EXT} = P_{ICPL}$ then $\Delta P = 0$ and the movable element 6 is restored to its balanced position. The balanced position of movable element 6 relative to the body 5 is indicated by a shoulder stop in FIG. 1, but other physical or electromagnetic fiducials are possible. A displacement of 6 relative to 5 can be made to cause changes in some predetermined physical, electrical, or magnetic characteristic or parameter of the sensor. Those changes can be detected by an external detection system 10 which is coupled to the implanted sensor by electromagnetic, acoustic, or other means across the skin, but not through the skin as by a tube or wire. The balance position may be predetermined and calibrated during construction so that it can be easily recognized after implantation by some known value of an electrical or mechanical characteristic of the sensor. Alternatively, with a mechanical stop to interrupt the downward movement of 6 relative to 5 as in FIG. 1, pressing on the skin just above diaphragm 7' will bring the sensor into its balanced condition and provides an instant zero-point calibration and check of the sensor and detector systems $\Delta P=0$ reference long after implantation. In operation external detector 10 interrogates the implanted sensor and determines if a balanced condition, $\Delta P=0$, or imbalanced condition, $\Delta P\neq 0$, exists in the sensor. With elevating intracranial pressure $\Delta P$ will become more positive temporarily. This will be detected by 10 and $P_{EXT}$ will be increased by an external pressurizer attached to the pressure applicator 11 until detector 10 detects a balanced condition $\Delta P=0$ at which point $P_{EXT}=P_{ICP}$ and may be recorded or read out. No particular calibration of $\Delta P$ versus displacement of element 6 relative to the frame is necessary although this may be built-in by spring loading 6, for added flexibility of measurement. The pressure balance method described here reduces the degree of complexity of the transsensor construction to only that necessary to detect deviations from a balance position rather than a calibrated pressure versus displacement characteristic. Thus, the burden of accurate pressure detection instrumentation lies external to the body where it is easily implemented. Two membranes 7 and 7' are shown in FIG. 1, however, as shown below, one membrane may be sufficient as long as it allows proper communication of $P_{ICP}$ and $P_{EXT}$ to movable element 6. Common implementations of the coupling of the motion of 6 to the external detector 10 are by use of a passive L-C circuit; this will be discussed below.

Referring to FIG. 2, a specific embodiment of the basic invention concepts of FIG. 1 is shown. The cylindrical body 5 comprises an insulating plastic such as nylon or "Lexan" and has an upper flange so that it seats in a standard burr hole in the skull 4. A fixed coil 12 and capacitor 13 are embedded in the body 5 to form a parallel L-C tank circuit. A magnetic slug 14 moves in a cylindrical hole through the body 5 and is attached to a coaxial cylinder 15, made of a non-magnetic material to the movable element 6 of FIG. 1. The two diaphragms 7 and 7' are made of thin flexible plastic material, may be convoluted for added flexibility, sealed to the body 5, and contact the ends of cylinders 14 and 15. The diaphragms 7 and 7' plus cylinders 14 and 15 form a dual motion-coupled membrane system with end-for-end symmetry such that $P_{ICP}$ is felt on one end, $P_{ATM}$ is communicated through the intact skin is felt on the other end, and the external force on the cylinders 14 and 15 is directly proportional to the difference $\Delta P=P_{ICP}-P_{ATM}$. When $P_{ICP}$ is greater than $P_{ATM}$, the magnetic slug 14 will move upward relative to coil 12 thus changing the inductance of the coil magnetic slug system. This in turn will cause a change in the resonant frequency of the L-C tank circuit, which is detected outside the body by an external detector system 10 described below. The coaxial cylinder 15 of non-magnetic material is attached to the ferrite and is shown here to have a stop-flange which comes against a shoulder in the frame 12 when the pressure balance $\Delta P=0$ is attained, as shown, and this will correspond to a balanced condition frequency $f_o$ of the resonant circuit. In operation the external pressurizer-control system will increase $P_{EXT}$ in the region 8 just above the sensor until the external detector determines that the frequency $f_o$ is reached; and thus $P_{EXT}$ equals $P_{ICP}$.

Referring to FIG. 3 means of detecting, tracking, and reading out the intracranial pressure $P_{ICP}$ are illustrated. The resonant L-C circuit in the implanted sensor 16 is coupled electromagnetically to the external detection system which comprises an antenna-oscillator 17 and a signal analyzing circuit and balance pressure detector 18. The oscillator in 17, operating typically at 10 to 100 Mega Hertz, is frequency swept at an audio rate. It experiences a power dip at the sensor's resonant frequency and the analyzer circuit 18 detects this dip and generates an output signal proportional to the associated resonant frequency. Such "grid-dip" oscillator detectors are well known and need not be described in detail here. The pressurizer-control system consists of a source of fluid 19 under pressure $P_{EXT}$ which is connected by a tube to pressure cuff 11, a pressure control means 20 for varying $P_{EXT}$ in 19 and 11, and a means 21 of measuring and reading out the pressure in 19. The pressure control means 20 would increase the pressure in 19, and thus $P_{EXT}$ applied to sensor 16 through the skin, until signal analyzer 18 detects that the frequency corresponding to a pressure balance on the sensor has been reached. At this point $P_{ICP}=P_{EXT}$ and is readout of 21. Pressure controller 20 may be manually operated or coupled to the output of 18 for automatic tracking of $P_{ICP}$. The pressure cuff 11 can be a flexible bag integrally attached to 17.

Figure 2:
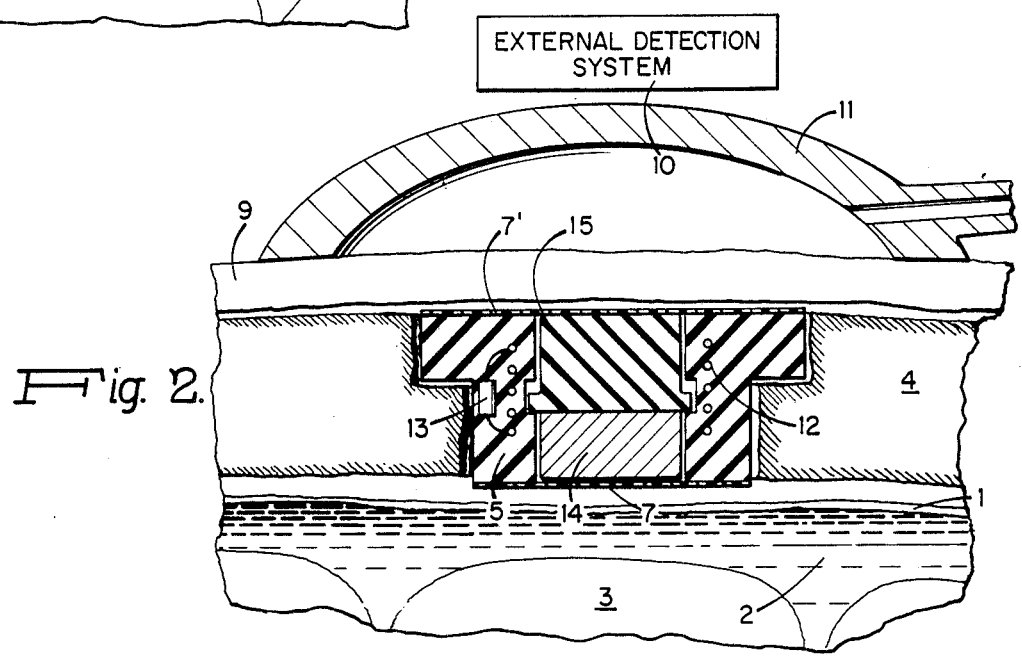
FIG. 2 shows a view in vertical section of a more specific design of the invention concept of FIG. 1 involving a passive L-C resonant circuit in the sensor.

There are several other notable novel features and ancillary points to be made about the design of FIG. 2. End-for-end symmetry of the dual motion-coupled diaphragm system, convoluted flexible diaphragms, and the very small innerspace $V_{IN}$ which is required only for wall clearance of the cylinders 14 and 15 eliminate drift due to diaphragm permeability, aberrations due to barometric pressure change, and hazard of rupture during air travel. If the innerspace volume $V_{IN}$ is initially filled with air and if diffusion of this gas outward and of fluid inward after implantation cause a reduced pressure $P_{IN}$ in $V_{IN}$ then because of end-for-end symmetry of 7, 7', 14 and 15 the forces on diaphragms 7 and 7' will be the same function of $P_{ICP}-P_{IN}$ and $P_{ATM}-P_{IN}$, and thus the net force, and associated displacement, of cylinder 14 and 15 will depend only on $\Delta P=P_{ICP}-P_{ATM}$ and not on $P_{IN}$. Should a sudden change $\delta P_{ATM}$ in barometric pressure, $P_{ATM}$, occur as in air flight the change in $V_{IN}$ will be $$\delta V_{IN} \approx -[(\delta P_{ATM})/P_{ATM}]V_{IN}$$

and if $V_{IN}$ is very small, so will be $\delta V_{IN}$. Thus the perturbation on and danger of rupturing of diaphragms 7 and 7' will be accordingly small, and again end-for-end symmetry will cancel any effect on the detection of $\Delta P$. The same argument applies to changes in $P_{IN}$ or $V_{IN}$ because of changes in surrounding temperature. The novel features of the application of an external balancing pressure to the sensor through the skin and the provision of a shoulder stop of 14 and 15 against the body 5 at equilibrium position, not only allow an instant zero pressure reference check, but also insures an instant check of the operation of the entire system and correction to any temperature dependent variations in the electro-mechanical characteristics of the sensor. The coil 12 and capacitor 13 can easily be selected for negligible temperature drift and high resonant Q. The cylinders 14 and 15 can be teflon coated and axially suspended on diaphragms 7 and 7' so that friction is minimized and the static and dynamic response and sensitivity are maximized. The design has been demonstrated in implantations to detect differences in intracranical pressure of less than 5 mm of $H_2O$ and to record easily the rapid pressure variations due to heart beat and respiration, these being important clinical indications of a working system which previous designs cannot achieve. The diaphragms 7 and 7' may be arranged co-planar with the dura 1 and scalp 9, respectively, during equilibrium so that surface tension effects of the latter are eliminated and fibrosis of the dura will not occur in long implantations, a problem which has plagued previous designs. A range of clinically observed pressures can be measured with complete linearity. The sensor is cosmetically inobtrusive, lying flat with the skull 4. The design of FIG. 2 can be made less than ½ inch in diameter and as shallow as 3 to 11 mm total height, making them adaptable to infants or small animals as well as adults. The design is intrinsically simple for high volume, low cost manufacture. It can be made of biocompatible material and covered with a thin silicone rubber enclosure.

Figure 1:
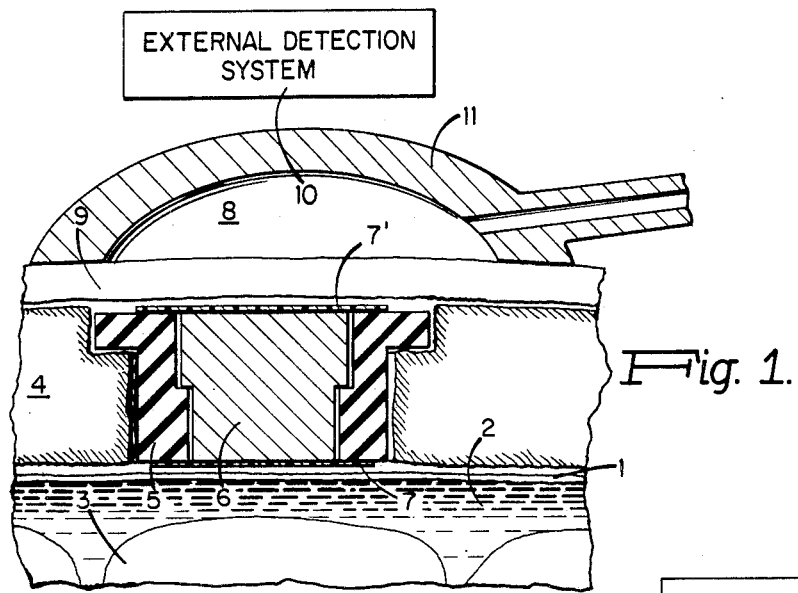
FIG. 1 shows a schematic, vertical sectional view of an implanted pressure sensor and related external systems being used to measure intracranial pressure in a living human being.
Figure 3:
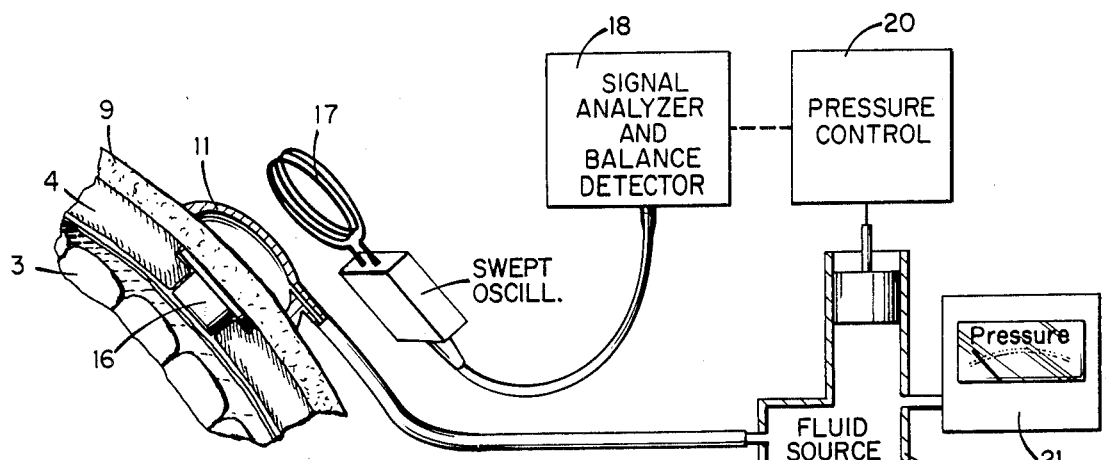
FIG. 3 illustrates implementation of the external detection and external pressurizer-control systems relative to the implanted sensor.

It is understood that many variations of the basic concepts disclosed in FIGS. 1, 2 and 3 are possible and included in this disclosure. The sensor may have only one diaphragm, which feels $P_{ICP}$ on one side and $P_{ATM}$ on the other. The movable element, equivalent to 6 in FIG. 1, may be attached to the single diaphragm and the displacement of it and the diaphragm is detected externally. In the dual motion-coupled diaphragm design, the diaphragms 7 and 7' may be stacked as in FIG. 1, but located at more remote separation. The coupling element 6 may be a rigid mechanical means such as a cylinder or linkage, or may be a fluid transmitted through the body by a tube or channel. The physical characteristic of the sensor which is changed and detected with change of differential pressure $\Delta P = P_{ICP} - P_{EXT}$ may be diverse, and accordingly, so may be the detection means. For example, referring to FIG. 1, the body 5 and movable element 6 may be scatterers or absorbers of mechanical, acoustic, or ultrasonic waves or of electromagnetic waves such as micro waves or infrared radiation and the external detector system 10 may involve a source, interferometer, echo detector, frequency or amplitude detector of these waves by which the balance condition of 6 relative to 5 may be detected. Unlike the design of FIG. 2 the sensor may contain active circuits with stored energy cells or induction power circuits. Many variations of the passive L-C circuit system of FIGS. 2 and 3 are possible, involving other kinds of variable inductors, variable capacitors, both variable inductors and capacitors, or variable resistors to change the resonant frequency or impedance with pressure. Yet another type of electromagnetic detection of the balance condition would be a simple pair of mechanical electric contacts which close when the $\Delta P = 0$ and open when $\Delta P \neq 0$, thus completing a passive or active circuit which is detected externally by electromagnetic means. Wide latitude is possible in choice of geometry, size, configuration of components, coil and ferrite geometrics, and frequency of the design of FIG. 2. The magnetic slug may be replaced by a conductive metal slug to achieve induction change by eddy current detuning. The diaphragm or diaphragms may be convoluted as a speaker or rolling diaphragm or as a usual cylindrical bellows to achieve flexibility. The diaphragm may be metal or metal-coated or made of a variety of strong, impermeable, and flexible materials. Initially, the inner spaces of the sensor may or may not contain fluid. If fluid is used to fill the inner spaces or to act as diaphragm coupling, a simple way of insuring that its amount will remain constant is to make it a water solution of the same ionic concentration as the cerebrospinal fluid and intracellular fluid. In this way, the osmotic pressures are equal inside and outside the sensor and the net diffusion flow across the diaphragms will be zero.

Figure 4:
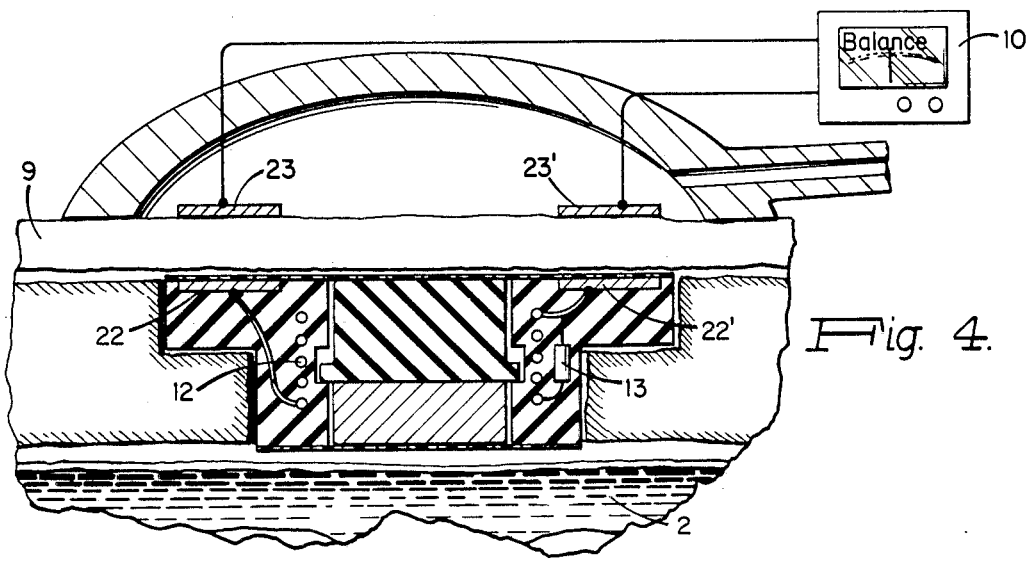
FIG. 4 illustrates capacitive transcutaneous coupling across the skin to an implanted sensor similar to that in FIG. 2.
Figure 5:
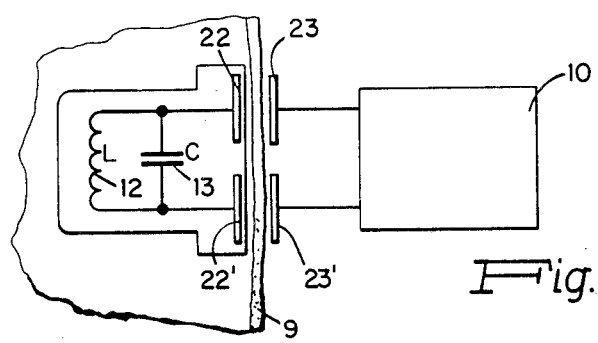
FIGS. 5, 6, 7 and 8 illustrate other sensor and transcutaneous coupling methods.

Referring to FIGS. 4, and 5, an example is shown of a sensor which incorporates an L-C resonant circuit similar to that in FIG. 2 but a different method of electromagnetic coupling across the skin 9 to the external detector system 10. The coupling method is transcutaneous capacitive coupling and is done by area electrodes 22 and 22' near the upper surface of the sensor. These are in proximity to electrodes 23 and 23', respectively, on the skin 4. At the L-C resonant frequency the capacitive reactance of these pairs of adjacent electrodes is small, and thus one can use the resonant frequency of the implanted L-C circuit to determine the frequency of oscillation of an external strongly coupled oscillator housed in 10. This frequency can then be used to indicate the pressure balance condition and the intracranial pressure as discussed above.

It is understood that variants of the transcutaneous coupling scheme of FIGS. 4 and 5 are assumed in this disclosure. For example, whereas in FIGS. 4 and 5 an inductor L and capacitor C are built into the sensor, either one of which or both of which may vary with pressure, it is also possible that only the pressure sensing inductor L, or capacitor C, may be in the implanted sensor, and that the other element of the L-C circuit, C or L respectively, may be in the external system 10 along with the strongly coupled oscillator.

Figure 6:
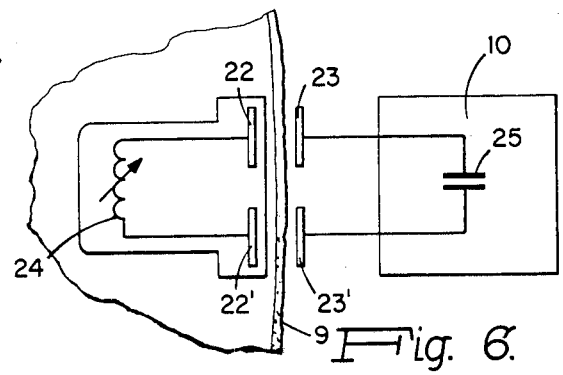

Referring to FIG. 6 the variable pressure sensing inductor 24 is coupled transcutaneously by area electrode pairs 22 and 22' and 23 and 23' to an external capacitor 25 which is integrated into the active external oscillator system that is contained in the external detection system 10. The frequency of oscillations of the external oscillator in 10 is determined by the L-C circuit made up of 24 and 25 and thus determines the balance conditions and intracranial pressure which is read out by 10.

Figure 7:
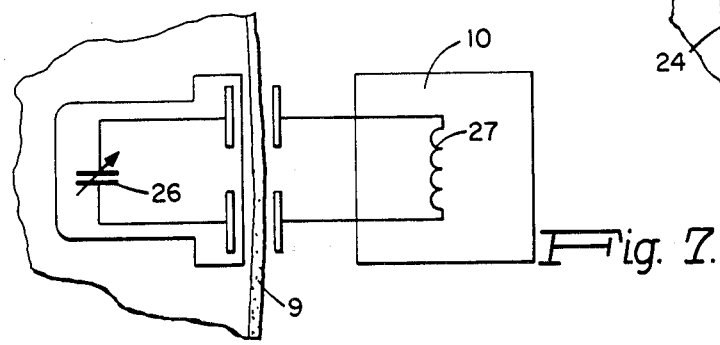

Referring to FIG. 7, the implanted sensor contains the pressure sensitive capacitor 26, and the external active oscillator in 10 contains the complementary inductor 27.

Figure 8:
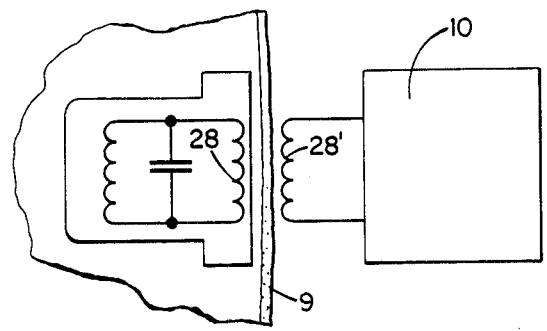

Referring to FIG. 8, the transcutaneous coupling is shown to be inductive rather than capacitive. The implanted L or C may be pressure sensitive, or the implant may contain only L or only C analogously to FIG. 6 and FIG. 7. The implanted coil 28 is coupled to external coil 28', thus achieving the necessary coupling through the skin to the external oscillator in 10. Again, as in designs of FIGS. 5, 6 and 7 the frequency of the external oscillator is determined by the L-C value of the pressure sensitive tank circuit.

Other embodiments of the basic designs disclosed above can be devised for other types of pressure measurements within the body and head. To take as illustrative examples in the case of measuring intracranial pressure, the present invention can be used in conjunction with other functional devices, such as catheters, valves, shunts, flushing devices, reservoirs, filters, anti-siphon devices, and so one, to form a more diverse or multipurpose intracranial pressure monitoring and control system. Some important illustrations are given below.

Referring to FIG. 9, the invention is shown connected to a ventricular catheter 29, which penetrates the brain 3 to the depth of the ventrical space 30 and samples the cerebrospinal fluid 31 therein through the holes 32. This device would then measure intraventricular fluid pressure. The catheter is usually made of silicone rubber and is an integral continuation of the encapsulation of the pressure sensor. Some variations in the designs of FIGS. 1 and 2 are also included in FIG. 9. A single diaphragm 7 is used and attached to a ferrite or magnetic cylinder 14 and a thinner geometry of the coil 12 and sensor body 5. In the pressure balanced position the top of the magnetic cylinder 14 is coplanar with the outer table of the skull and its lower rim rests on a shoulder in the body 5. In operation, the hydrostatic pressure of the cerebrospinal fluid acts directly on the bottom side of this single membrane and it must be balanced by an equal external pressure applied through the pressure cuff 11, at which point the resonant L-C circuit's frequency is the balanced frequency $f_o$ as detected by the extend detection system 10.

Referring to FIG. 10, a sensor of low profile as in FIG. 9 is used with a cathetor 29 which reaches into the ventricular space in the brain and probes the cerebrospinal fluid pressure there. This fluid presses on the lower membrane 7 which is attached to the magnetic slug 14 which in turn is coupled to the upper membrane 7'. Membrane 7' is coplanar with the scalp in the balanced position. The cerebrospinal fluid may be channelled further through tube 33 to a fluid valve 34. Should an excess intraventricular pressure exist, the valve can be opened and the fluid shunted off into the blood stream or elsewhere through the exit tube 35. Shunt valves and ventricular catheter combinations already exist, however, the combination of these with the pressure sensor as in FIG. 10 is a new and unique combination made possible by the present invention concept. Enabling the brain pressure to be read by the sensor is an essential check on the patient status and the proper functioning of the valve. The very low profile of the sensor which is possible with this invention design is of critical importance in such implementations as in FIGS. 9 and 10. It is readily possible to automatically monitor the pressure in an arrangement like that in FIG. 10 and also automatically control the operation of the shunt valve 34 according to whether the pressure is too high or not. It is assumed that such extrapolations and combinations in usage of the present invention are included in the present disclosure.

Figure 11:
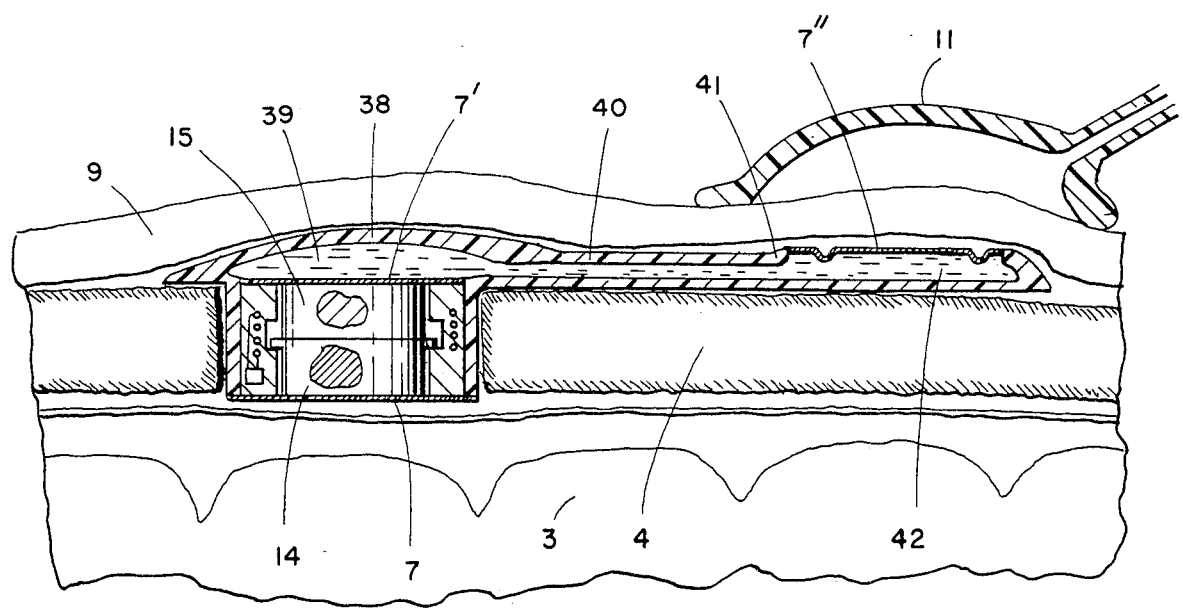
FIG. 11 illustrates another embodiment in which the external balancing pressure is communicated to an upper, flexible diaphragm through a closed fluid system.

Referring to FIG. 11, another embodiment of the invention is illustrated for which the external balancing pressure communicated to the upper flexible diaphragm is supplied by a closed fluid system, rather than directly across the adjacent skin as in FIG. 2. A semi-rigid housing 38 covers diaphragm 7' with a space 39 between them. The housing 38 is connected by a tube 40 to a second housing 41 which lies flat against the skull and which is covered on its upper side by a third flexible diaphragm 7'', thus communicating with the skin above it and thereby with the external pressure on the skin applied by the pressure cuff 11. A fluid fills the volume 39, the tube 40, and the space 42 inside 41. The system is then a triple motion-coupled diaphragm arrangement. The first two diaphragms 7 and 7' plus the magnetic piston 14 and 15 act the same as described above, and the differential pressure on 7 and 7' is sensed by an external detector system. The pressure applied against 7' is now transmitted to it by the fluid filled system comprising 38, 40, 41 and 7''. The applied external pressure on the skin above 7'' will also be transmitted to 7'; and this could serve (a) to zero the magnetic piston 14 plus 15 and thus check the zero-point of the entire system, or (b) to supply a known and calibrated external pressure to 7' so as to balance the internal pressure on 7 and thus measure it by the pressure nulling method.

A configuration similar to that in FIG. 11 is possible where only two flexible diaphragms are used and the differential pressure implant is catheterized to measure a remote pressure in the ventricles, as was illustrates in FIGS. 9 and 10.

Figure 12:
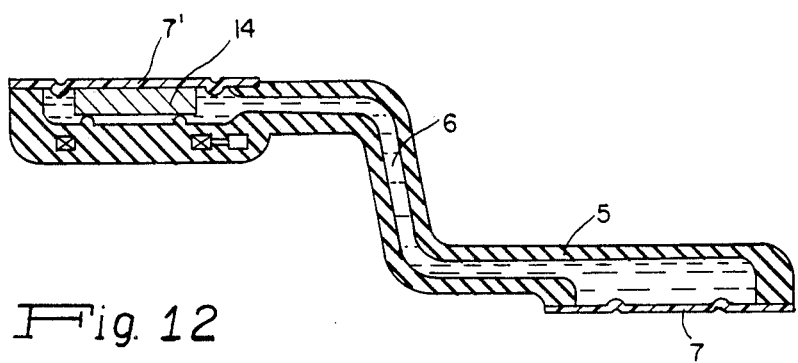
FIG. 12 illustrates another embodiment of the invention utilizing fluid motion coupling between two diaphragms.

FIG. 12, illustrates another embodiment of the invention. The same reference numerals have been employed to indicate like components of the differential pressure sensor. The embodiment of FIG. 12 depicts the two diaphragms 7 and 7' fluidly connected by means of a tube 5. The tube filled with an incompressible fluid 6 that provides motion coupling between diaphragms 7 and 7'.

Diaphragm 7 is a convoluted planar diaphragm that is substantially the same as diaphragm 7'.

Having described in detail various embodiments of my invention, it will now be apparent to those skilled in the art that numerous modifications can be made therein without departing from the scope of the invention as defined in the following claims. For example, external manipulation of the diaphragm can be achieved by fluidly coupling a pressure source to the diaphragm by means of a fluid filled tube extending through the skin to the diaphragm.

What I claim and desire to secure by Letters Patent of the United States is:

1. A differential pressure sensor adapted for implantation beneath the skin in the living body and for in vivo calibration after implantation, said sensor comprising:
   a. a housing having means defining an opening, extending therethrough;
   b. a first flexible diaphragm extending across the housing opening and being secured with respect to said housing, at least a portion of said first flexible diaphragm defining a portion of the exterior surface of said sensor and being positioned so that after implantation beneath the skin said portion of said first flexible diaphragm is in mechanical pressure communication with the skin and whereby pressurs external to the body can be communicated mechanically across the intact skin to said first flexible diaphragm;
   c. a second flexible diaphragm extending across the housing opening and being secured with respect to said housing, said diaphragms and opening defining means defining a chamber within said sensor and the side of said second flexible diaphragm that is external to said chamber being positioned to be in contact with and in mechanical pressure communication with a bodily medium, the pressure of which is to be sensed when said sensor is implanted in the living body;
   d. solid coupling means located within said chamber and secured to both of said flexible diaphragms for coupling the motion of one of said flexible diaphragms to the other of said flexible diaphragms so that, when said sensor is implanted in the living body, changes in the difference in pressures in said bodily medium and on said exterior portion of said first flexible diaphragm will cause motion of said flexible diaphragms and said solid coupling means;
   e. contact means connected to said housing for contacting (i) at least one of said diaphragms or (ii) said solid coupling means thereby defining a mechanical contact reference position with respect to said housing of (i) at least one of said diaphragms or (ii) of said solid coupling means for a predetermined pressure relationship between said pressure in communication with said two flexible diaphragms when said sensor is implanted in the living body; and, f. means having a preselected, detectable parameter that is detectable by detection means located outside the living body, said means having a preselected, detectable parameter being at least in part cooperatively connected to and movable with at least one of said flexible diaphragms or said solid coupling means so that said preselected detectable parameter will change with movement of displacement of (i) at least one of said flexible diaphragms or (ii) of said solid coupling means and the value of said preselected, detectable parameter can be detected at said mechanical contact reference position, said at least one flexible diaphragm or said solid coupling means and said means having a preselected detectable parameter being so constructed and cooperatively connected that the value of said preselected detectable parameter changes upon a change from said predetermined pressure relationship; whereby, when said sensor is implanted beneath the skin, (i) at least one of said flexible diaphragms or (ii) said solid coupling means can be driven to said mechanical contact reference position by a pressure external to the living body applied to the skin adjacent to said sensor, and said preselected detectable parameter can be determined at said mechanical contact reference position after implantation, and whereby the magnitude of the external pressure applied to the skin that is required to drive (i) at least one of said flexible diaphragms or (ii) said solid coupling means to said mechanical contact reference position is a function of the pressure in said bodily medium.

2. The sensor of claim 1 wherein said predetermined pressure relationship is the balance of said pressures.

3. The differential pressure sensor of claim 1 wherein said means having a preselected detectable parameter comprises a resonant electrical circuit which includes a coil and a capacitor which are in part fixed relative to said housing and also comprises a tuning element for at least one of said coil or capacitor, said tuning element moving with said flexible diaphragms, whereby a characteristic response parameter of said resonant electrical circuit is changed by the movement of said tuning element and whereby said characteristic response parameter is detectable by electronic apparatus outside the living body.

4. The differential pressure sensor of claim 3 wherein said tuning element includes a magnetic material which is attached to at least one of said flexible diaphragms or said solid means and which moves upon movement of said diaphragms in such a way that the inductance of said coil is varied in accordance with the relative displacement of said magnetic material to said coil.

5. The differential pressure sensor of claim 4 wherein said coil is fixed with respect to said housing and wherein said mechanical contact reference position defining means defines a mechanical stop reference position of said magnetic material with respect to said coil.

6. The differential pressure sensor of claim 3 wherein the motion of said tuning element varies the capacitance of said capacitor in response to the movement of at least one of said diaphragms or of said solid coupling means and thereby changes the characteristic response parameter of said resonant circuit.

7. The differential pressure sensor of claim 3 wherein said resonant electrical circuit is a parallel resonant circuit and wherein said preselected, detectable parameter is the resonant frequency of said parallel resonant circuit.

8. The differential pressure sensor of claim 3 further comprising first and second area electrodes electrically connected to said coil, third and fourth area electrodes positioned with respect to said first and second area electrodes, respectively, for capacitive coupling thereto, and means electrically connected to said third and fourth area electrodes for detecting said parameter and any variation therein.

9. The differential pressure sensor of claim 1 wherein said preselected, detectable parameter means includes means for spring-loading at least one of said diaphragms, said spring-loading means having a known spring constant.

10. The differential pressure sensor of claim 1 further comprising means for detecting said preselected, detectable parameter and any variation therein.

11. The differential pressure sensor of claim 1 wherein said means solid for motion coupling said first and second diaphragms includes a rigid mechanical coupling between said diaphragms.

12. The differential pressure sensor of claim 11 wherein said first and second diaphragms have equal areas and said rigid mechanical coupling has symmetrical diaphragm contacting ends to provide end-for-end pressure symmetry.

13. The apparatus of claim 1, wherein said two flexible diaphragms are substantially planar flexible diaphragms.

14. The apparatus of claim 1, wherein said two flexible diaphragms are convoluted to achieve flexibility.

15. An in vivo pressure detecting system comprising:
a. a differential pressure sensor adapted for implantation in a living body, said sensor comprising:
(1) a housing having means defining an opening extending therethrough;
(2) flexible diaphragm means extending across said housing opening and being fluid pressure sealed with respect to said housing, said flexible diaphragm means communicating with pressures in two separate regions external to the sensor that are separated by the flexible diaphragm means with the pressure in one of the regions being an internal bodily pressure when the sensor is implanted in a living body;
(3) contact means connected to said housing for contacting said flexible diaphragm means thereby defining a mechanical contact reference position of said flexible diaphragm means with respect to said housing for a predetermined pressure relationship in said regions when said sensor is implanted in the living body; and,
(4) means having a preselected, detectable parameter that is detectable by detection means located outside the living body, said means having a preselected, detectable parameter being at least in part cooperatively connected to and movable with said flexible diaphragm means so that said preselected detectable parameter will change with movement of said flexible diaphragm means and the value of said preselected detectable parameter can be detected at said mechanical contact reference position, said flexible diaphragm means and said means having a preselected, detectable parameter being so constructed and cooperatively connected that the value of said preselected detectable parameter changes upon a change from said predetermined pressure relationship; whereby, when said sensor is implanted beneath the skin and flexible diaphragm means can be driven to said mechanical contact reference position by a pressure external to the living body applied to the skin adjacent to said sensor and said preselected detectable parameter can be determined at said mechanical contact reference position after implantation, and whereby the magnitude of the external pressure applied to the skin that is required to drive said flexible diaphragm means to said mechanical contact reference position is a function of the internal bodily pressure;

b. a controllable pressure source means external to the living body for establishing said predetermined pressure relationship and for applying and measuring the external pressure applied to the skin and, c. means for detecting said sensor parameter and the value of the parameter at the reference position and any variation therefrom when said sensor is implated in a living being, said detecting means being located externally of the living body and without any connection to said sensor which requires a break in the skin of the living body.

16. The system of claim 15 wherein at least a portion of said controllable pressure source means and said sensor parameter detecting means comprise an integral unit.

17. The sensor of claim 15 wherein said means having a preselected, detectable parameter comprises a scatterer of ultrasonic radiation which moves with said flexible diaphragms and wherein said means for detecting said sensor parameter comprises a source and detector of ultrasonic radiation, whereby the movement of said scatterer alters the characteristic of the scattered ultrasonic radiation from said source that can be detected by said detector.

18. The apparatus of claim 15, wherein said flexible diaphragm means is a substantially planar flexible diaphragm.

19. The apparatus of claim 15, wherein said two flexible diaphragms are convoluted to achieve flexibility.

20. An in vivo pressure detecting system comprising:
a. a differential pressure sensor adapted for implantation in a living body and in in vivo calibration after implantation, said sensor comprising:

(1) a housing having means defining an opening extending therethrough;

(2) a first flexible diaphragm extending across said housing opening and being secured with respect to said housing, at least a portion of said first flexible diaphragm defining a portion of the exterior surface of said sensor and being positioned so that after implantation beneath the skin said portion of said first flexible diaphragm is in mechanical pressure communication with the skin and whereby pressures external to the body can be communicated mechanically across the intact skin to said first flexible diaphragm;

(3) a second flexible diaphragm extending across the housing opening and being securd with respect to said housing, said flexible diaphragms and opening defining means defining a chamber within said sensor and the side of said second flexible diaphragm that is external to said chamber being positioned to be in contact with and in mechanical pressure communication with a bodily medium, the pressure of which is to be sensed when the sensor is implanted in a living body;

(4) solid coupling means located within said chamber and secured to both of said flexible diaphragms for coupling the motion of one of said flexible diaphragms to the other of said flexible diaphragms so that when said sensor is implanted in the living body, changes in the difference in pressures in said bodily medium and on said exterior portion of said first flexible diaphragm will cause motion of said flexible diaphragms and said solid coupling means;

(5) contact means connected to said housing for contacting (i) at least one of said diaphragms or (ii) said solid coupling means thereby defining a mechanical contact reference position with respect to said housing of (i) at least one of said diaphragms or (ii) of said solid coupling means for a predetermined pressure relationship between said pressures in communication with said two flexible diaphragms when said sensor is implanted in the living body;

(6) means having a preselected, detectable parameter that is detectable by detecting means located outside the living body, said means having a preselected, detectable parameter being at least in part cooperatively connected to and movable with at least one of said flexible diaphragms or said solid coupling means so that said preselected detectable parameter will change with movement of (i) at least one of said diaphragms or (ii) of said solid coupling means and the value of said preselected, detectable parameter can be detected at said mechanical contact reference position, said at least one flexible diaphragm or said solid coupling means and said means having a preselected, detectable parameter being so constructed and cooperatively connected that the value of said preselected, detectable parameter changes upon a change from said predetermined pressure relationship; whereby said sensor is implanted beneath the skin, (i) at least one of said flexible diaphragms or (ii) said incompressible means sensor can be driven to said mechanical contact reference position by a pressure external to the living body applied to the skin adjacent to said sensor, and said preselected detectable parameter can be determined at said mechanical contact reference position after implantation, and whereby the magnitude of the external pressure applied to the skin that is required to drive (i) at least one of said flexible diaphragms or (ii) said solid means sensor to said mechanical cntact reference position is a function of the pressure in said bodily medium;

b. controllable pressure source means external to the living body adapted to apply and measure an external pressure to the intact skin adjacent to said sensor, and thereby transmitting said external pressure to said first flexible diaphragm for establishing said predetermined pressure relationship; and, c. means for detecting said preselected, detectable parameter and the value of the parameter at said mechanical contact reference position and any variation therefrom when said sensor is implanted in a living body, said detecting means being located externally of the living body and without any connection to said sensor which requires a break in the skin of the living body.

21. The pressure detecting system of claim 20 wherein one end of said pressure sensor comprises:
defines a fluid containing chamber, said first flexible diaphragm defines a flexible wall of said fluid containing chamber, said housing opening means comprises means for fluid pressure coupling the fluid containing chamber to said second flexible diaphragm; said incompressible means comprises a fluid filling said fluid containing chamber; whereby when said pressure sensor is implanted beneath the skin of the living body with said flexible chamber wall being in mechanical contact with the skin then said external pressure exerted on the skin in proximity to said flexible chamber wall is transmitted to said second diaphragm.

22. The pressure detecting system of claim 20 wherein the pressure source comprises:
a. means defining a fluid containing chamber having a flexible, substantially planar wall;
b. means for fluid pressure coupling the chamber to said first diaphragm;
c. a fluid filling the chamber;
said fluid containing chamber being located externally of the living body.

23. The pressure detecting system of claim 20 further comprising a catheter fluidly coupled to said second diaphragm to communicate thereto pressure of internal bodily fluids.

24. The pressure detection system of claim 20 further comprising a first catheter fluidly coupled to the second diaphragm, a shunt valve fluidly coupled at one end to said second diaphragm, and a second catheter fluidly coupled to the other end of said shunt valve whereby said sensor is adapted to be in series with and measures the pressure in a conduit of an internal bodily fluid.

25. The pressure detecting system of claim 20 wherein said means having a preselected variable parameter comprises a resonant electrical circuit which includes a coil and a capacitor.

26. The pressure detecting system of claim 25 wherein said means for motion coupling said diaphragms includes a magnetic material which moves upon movement of the diaphragms in such a way that the inductance of said coil is varied in accordance with the relative displacement of the magnetic material, to the coil.

27. The pressure detecting system of claim 26 wherein said coil is fixed with respect to said housing and wherein said reference position defining means defines a reference position of said magnetic material with respect to said coil.

28. The pressure detecting system of claim 25 further comprising means for varying the capacitance of said capacitor in response to the movement of at least one of said diaphragms or of said motion coupling means.

29. The pressure detecting system of claim 25 wherein said resonant electrical circuit is a parallel resonant circuit and wherein said variable parameter is the resonant frequency of the parallel resonant circuit.

30. The pressure detecting system of claim 25 further comprising first and second area electrodes electrically connected to said coil, third and fourth area electrodes positioned with respect to said first and second area electrodes, respectively, for capacitive coupling thereto, said third and fourth area electrodes being external to the living body and electrically connected to said means for detecting said parameter and any variation therein.

31. The pressure detecting system of claim 30 wherein said capacitor is external to the living body and is electrically connected to said third and fourth area electrodes.

32. The pressure detecting system of claim 30 wherein said coil is external to the living body and is electrically, connected to said third and fourth area electrodes.

33. The pressure detecting system of claim 20 wherein said means having a variable parameter includes means for spring-loading at least one of said diaphragms, said spring-loading means having a known spring constant.

34. The pressure detecting system of claim 20 further comprising means for detecting said parameter and any variation therein.

35. The pressure detecting system of claim 20 wherein said means for motion coupling said first and second diaphragms includes a rigid mechanical coupling between said diaphragms.

36. The pressure detecting system of claim 35 wherein said first and second diaphragms have equal areas and said rigid mechanical coupling has symmetrical diaphragm contacting ends to provided end-for-end pressure symmetry.

37. The system of claim 20 wherein at least a portion of said controllable pressure source means and said sensor parameter detecting means comprise an integral unit.

38. The sensor of claim 20 wherein said means having a preselected, detectable parameter comprises a scatterer of ultrasonic radiation which moves with said flexible diaphragms and wherein said means for detecting said sensor parameter comprises a source and detector of ultrasonic radiation, whereby the movement of said scatterer alters the characteristic of the scattered ultrasonic radiation from said source that can be detected by said detector.

39. The apparatus of claim 20, wherein said two flexible diaphragms are substantially planar flexible diaphragms.

40. The apparatus of claim 20, wherein said two flexible diaphragms are convoluted to achieve flexibility.

41. An in vivo pressure detecting system comprising:
a. a balanced differential pressure sensor adapted for implantation in a living body, said sensor comprising:
(1) a housing having means defining an opening extending therethrough;
(2) a flexible diaphragm extending across said housing opening and being fluid pressure sealed with respect to said housing, said diaphragm communicating with pressures in two separate regions external to the sensor that are separated by the flexible diaphragm with one side of the diaphragm communicating with a pressure source and the other side of the diaphragm communicating with an internal bodily pressure when the sensor is implanted in a living body;

(3) means for defining a reference position of said diaphragm with respect to said housing for a predetermined pressure relationship between the pressure of the pressure source and the internal bodily pressure;

(4) means having a preselected, detectable variable parameter that changes with displacement of said diaphragm means from the reference position upon a change from said predetermined pressure relationship;

b. pressure source means external to the living body for establishing said predetermined pressure relationship; and, c. means for detecting said sensor parameter and the value of the parameter at the reference position and any variation therefrom when said sensor is implanted in a living being, said detecting means being located externally of the living body and without any connection to said sensor which requires a break in the skin of the living body.

42. The pressure detecting system of claim 41 further including a pressure source comprising:
   a. means defining a fluid containing chamber having a flexible, substantially planar wall;
   b. means for fluid pressure coupling the chamber to said first diaphragm;
   c. a fluid filling the chamber;
said pressure source being implanted beneath the skin of the living body with the chamber wall being substantially co-planar with the surface of the skin whereby external pressure exerted on the skin in proximity to the wall is transmitted to one side of said diaphragm.

43. The pressure detecting system of claim 41 further including a pressure source comprising:
   a. means defining a fluid containing chamber having a flexible, substantially planar wall;
   b. means for fluid pressure coupling the chamber to said first diaphragm;
   c. a fluid filling the chamber;
said fluid containing chamber being located externally of the living body.

44. The pressure detecting system of claim 41 further comprising a catheter fluidly coupled to one side of said diaphragm to communicate thereto pressure of bodily fluids.

45. The pressure detection system of claim 41 wherein the pressure from said pressure source means is transmitted to the first diaphragm through adjacent intact skin and further comprising a first catheter fluidly coupled to the second diaphragm, a shunt valve fluidly coupled at one end to said second diaphragm, and a second catheter fluidly coupled to the other end of said shunt valve.

46. The pressure detecting system of claim 41 wherein said means having a preselected variable parameter comprises a resonant electrical circuit which includes a coil and a capacitor.

47. The pressure detecting system of claim 46 further comprising a magnetic material which moves with the diaphragm in such a way that the inductance of said coil is varied in accordance with the relative displacement of the magnetic material and the coil.

48. The pressure detecting system of claim 47 wherein said coil is fixed with respect to said housing and wherein said reference position defining means defines a reference position of said magnetic material with respect to said coil.

49. The pressure detecting system of claim 47 further comprising first and second area electrodes electrically connected to said coil, third and fourth area electrodes positioned with respect to said first and second area electrodes, respectively, for a capacitive coupling thereto, said third and fourth area electrodes being external to the living body and, electrically connected to said means for detecting said parameter and any variation therein.

50. The pressure detecting system of claim 49 wherein said capacitor is external to the living body and is electrically connected to said third and fourth area electrodes.

51. The pressure detecting system of claim 49 wherein said coil is external to the living body and is electrically connected to said third and fourth area electrodes.

52. The pressure detecting system of claim 46 further comprising means for varying the capacitance of said capacitor in response to the movement of said diaphragm.

53. The pressure detecting system of claim 46 wherein said resonant electrical circuit is a parallel resonant circuit and wherein said variable parameter is the resonant frequency of said parallel resonant circuit.

54. The pressure detecting system of claim 41 wherein said means having a variable parameter includes means for spring-loading at least one of said diaphragms, said spring-loading means having a known spring constant.

55. An in vivo differential pressure sensor adapted for implantation beneath the skin in the living body and for in vivo calibration after implantation, said sensor comprising:
   a. a housing having means defining an opening therethrough;
   b. a first flexible diaphragm having an interior side and an exterior side, said first flexible diaphragm extending across the housing opening at substantially one end thereof and being secured to said housing, at least a portion of said exterior side of said flexible diaphragm defining a portion of the exterior surface of said sensor and being positioned so that after said sensor is implanted beneath the skin said portion of said exterior side of said first flexible diaphragm is in mechanical pressure communication with the skin whereby pressures external to the living body can be communicated mechanically across the intact skin to said first flexible diaphragm;
   c. a second flexible diaphragm having an interior side and an exterior side, said second flexible diaphragm extending across said housing opening at substantially the other end thereof and being secured to said housing, said first and second flexible diaphragm interior sides and said housing opening defining a chamber within said sensor and, when said sensor is implanted in a living body, said exterior side of said second flexible diaphragm being positioned to be in contact with and in mechanical pressure communication with a bodily medium, the pressure of which is to be sensed;
   d. solid coupling means located within said chamber and secured to both of said flexible diaphragms for coupling the motion of one of said flexible diaphragms to the other of said flexible diaphragms, the motion of said flexible diaphragms being in response to changes in the difference in pressures on said exterior sides of said two flexible diaphragms;

e. contact means connected to said housing for contacting (i) at least one of said diaphragms or (ii) said solid coupling means thereby defining a mechanical contact reference position within said sensor and with respect to said housing of (i) at least one of said flexible diaphragms or (ii) said solid coupling means, said reference position corresponding to a predetermined pressure relationship between said pressure on the exterior side of the first flexible diaphragm and the pressure on the exterior side of the second flexible diaphragm; and, f. means having a preselected, detectable parameter that is detectable by detection means located outside the living body, said means having a preselected, detectable parameter being at least in part cooperatively connected to and movable with at least one of said flexible diaphragms or said solid coupling means so that said preselected, detectable parameter will change with movement of (i) at least a portion of one of said flexible diaphragms or (ii) said solid coupling means and the value of said preselected, detectable parameter can be detected at said mechanical contact reference position, said at least one flexible diaphragm or said solid coupling means and said means having a preselected, detectable parameter being so constructed and cooperatively connected that the value of said preselected detectable parameter changes upon a change from said predetermined pressure relationship; whereby said sensor is implanted beneath the skin, (i) at least one of said flexible diaphragms or (ii) said solid coupling means can be driven to said mechanical contact reference position to said mechanical contact reference position by a pressure external to the living body applied to the skin adjacent to said sensor, and said preselected detectable parameter can be determined at said mechanical contact reference position after implantation, and whereby the magnitude of the external pressure applied to the skin that is required to drive (i) at least one of said flexible diaphragms or (ii) said solid coupling means to said mechanical contact reference position is a function of the pressure in said bodily medium.

56. The apparatus of claim 55 wherein said mechanical contact reference position means comprises a mechanical stop for at least one of said flexible diaphragms or for said solid coupling means with respect to said housing.

57. The apparatus of claim 56 wherein said first and second flexible diaphragms are fluid pressure sealed with respect to said housing.

58. The apparatus of claim 55 wherein said mechanical contact reference position means includes electrode contacts that touch at a reference position relative to said housing of (i) of at least one of said flexible diaphragms or (ii) said solid coupling means, and said means having a preselected, detectable parameter includes circuit means within said sensor cooperative with said electrode contacts whereby the touching of said electrode contacts produces a detectable characteristic response of said circuit means.

59. The apparatus of claim 55 wherein said first and second flexible diaphragm interior sides and said housing opening define a single, undivided chamber.

60. The apparatus of claim 55 wherein said solid motion coupling means comprises a rigid mechanical coupling.

61. The apparatus of claim 55 wherein said solid motion coupling means comprises a rigid piston located within said chamber and connected between said flexible diaphragms.

62. The apparatus of claim 61, wherein the inner space of said chamber within said sensor that is not occupied by said rigid piston is filled with an ionic water solution which has similar osmotic pressure as bodily fluids, whereby the difference in osmotic pressures inside and outside of said sensor are equlized and whereby the transport of water and ions across said flexible diaphragms is reduced.

63. The apparatus of claim 55 wherein said mechanical reference position corresponds to the balance of said pressures on said exterior side of said two flexible diaphragms.

64. The apparatus of claim 55 wherein at least one of said flexible diaphragms or said motion coupling means is spring loaded with respect to said housing.

65. The apparatus of claim 55 wherein said first and second flexible diaphragms have substantially equal areas and symmetries to provide end-for-end pressure symmetry of said sensor.

66. The apparatus of claim 55 wherein at least one of said housing opening ends is planar and the flexible diaphragm secured to said planar opening end is substantially coplanar with said planar opening end at said predetermined pressure relationship to the pressures on said exterior sides of said flexible diaphragms.

67. The apparatus of claim 55 wherein said means having a preselected, detectable parameter comprises electronic circuit means, said detectable parameter being a characteristic response parameter of said electronic circuit means that is detectable by electromagnetic coupling to an electronic detection means located external to said living body.

68. The apparatus of claim 67 wherein said electronic circuit means includes an inductor and further comprises a magnetic material which moves relative to the inductor with movement of (i) at least one of said flexible diaphragms or (ii) said motion coupling means, such movement producing a displacement of said magnetic material relative to said inductor thereby varying the inductance of said inductor and thus varying said circuit characteristic response parameter.

69. The apparatus of claim 67 wherein said electronic circuit means include an inductor and further comprises a conductive material which moves relative to the inductor with movement of (i) at least one of said flexible diaphragms or (ii) said solid coupling means, such movement producing a displacement of said conductive material relative to the inductor thereby varying the inductance of said inductor and thus varying said circuit characteristic response parameter.

70. The apparatus of claim 67 wherein said electronic circuit means comprises a resonant electrical circuit which includes a coil and a capacitor, an element of said resonant circuit moving relative to another element of said resonant circuit upon movement of said flexible diaphragms so as to produce a change in said characteristic response parameter.

71. The apparatus of claim 70 wherein said coil is fixed with respect to said housing.

72. The apparatus of claim 70 wherein an element of said resonant circuit moves with said flexible diaphragms so as to vary the capacitance of said capacitor in response to the displacement of (i) at least one of said flexible diaphragm means or (ii) said solid coupling means, and thereby varying said characteristic response parameter of said resonant circuit.

73. The apparatus of claim 70 wherein said resonant electrical circuit is a parallel resonant circuit and wherein said preselected detectable parameter is the resonant frequency of said parallel resonant circuit.

74. The sensor of claim 55 wherein said means having a preselected, detectable parameter includes at least one of said flexible diaphragms.

75. The sensor of claim 55 wherein said means having a preselected, detectable parameter comprises a scatterer of ultrasonic radiation, which moves with said flexible diaphragms so that said motion can be detected by ultrasonic radiation source and detection apparatus located outside the living body.

76. The apparatus of claim 55, wherein said two flexible diaphragms are substantially planar flexible diaphragms.

77. The apparatus of claim 55, wherein said two flexible diaphragms are convoluted to achieve flexibility.

78. The sensor of claim 55 wherein said housing has a first and a second end such that the perimeter of said through opening in said housing at each of said two ends is substantially planar, said first flexible diaphragm being substantially planar when in its relaxed state and being secured to said planar perimeter at said first end and forming part of the external surface of said sensor, said second flexible diaphragm being substantially planar when in its relaxed state and being secured to said planar perimeter at said second end, each of said flexible diaphragms being substantially coplanar with its respective through opening perimeter when the pressures on said exterior sides of said flexible diaphragms are equal, said mechanical contact reference position comprising a stop means on said housing for the motion of said flexible diaphragms when the pressure on the exterior side of said first flexible diaphragm is equal to or greater than the pressure on the exterior side of said second flexible diaphragm, whereby when said sensor is implanted beneath the skin in the living body, said sensor is adapted so that said first flexible diaphragm is in mechanical contact with the skin and said second flexible diaphragm is in contact with a bodily tissue the pressure of which is to be sensed, and whereby surface tension force components of the skin and the bodily tissue in contact with said flexible diaphragms are reduced when the pressure on said external sides of said flexible diaphragms are equal.

79. An in vivo differential pressure sensor adapted for implantation beneath the skin in the living body and for in vivo calibration after implantation, said sensor comprising:

a. a housing having means defining an opening therethrough;
   b. first flexible diaphragm having an interior side and an exterior side, said first flexible diaphragm extending across the housing opening at one end thereof and being secured to said housing, at least a portion of said exterior side of first flexible diaphragm defining a portion of the exterior surface of said sensor and being positioned so that after said sensor is implanted beneath the skin said portion of said exterior side of said first flexible diaphragm is in mechanical pressure communication with the skin, whereby pressures external to the living body can be communicated mechanically across the intact skin to said first flexible diaphragm;
   c. a second flexible diaphragm having an interior side and an exterior side, said second flexible diaphragm extending across said housing opening at the other end thereof and being secured to said housing, said first and second flexible diaphragm interior sides together with said housing opening defining a chamber within said sensor and, when said sensor is implanted in a living body, said exterior side of said second flexible diaphragm being positioned to be in contact with and in mechanical pressure communication with a bodily medium, the pressure of which is to be sensed;
   d. a rigid piston located within said chamber, the rigid piston extending between and being secured to the interior sides of said flexible diaphragms, so that changes in said pressures on said exterior sides of said flexible diaphragms will cause a motion of said flexible diaphragms and said rigid piston, said piston including a magnetic material portion;
   e. parallel resonant circuit means comprising an inductor and a capacitor that are mounted within said housing so that the inductance of said inductor and thus the resonant frequency of said parallel resonant circuit means is varied in accordance with the position of the magnetic material portion relative to the inductor, the resonant frequency of said parallel resonant circuit means being detectable by detection apparatus located external to the living body, whereby said resonant frequency changes in accordance with changes in said pressures on said exterior sides of said flexible diaphragms; and,
   f. a mechanical stop for said piston against said housing when the pressures on said exterior sides of said flexible diaphragms are equal; whereby, when said sensor is implanted beneath the skin, said rigid piston can be driven to said mechanical stop by a pressure external to the living body applied to the skin adjacent to said sensor, and said resonant frequency can be detected at the position of said rigid piston at said mechanical stop after said sensor has been implanted in the living body, and whereby the value of the external pressure applied to the skin required to drive said rigid piston to said mechanical stop, as indicated by said resonant freqency, is equal to the pressure in said bodily medium.

80. The apparatus of claim 79, wherein the inner space of said chamber within said sensor that is not occupied by said rigid piston is filled with an ionic water solution which has similar osmotic pressure as bodily fluids, whereby the difference in the osmotic pressure inside and outside said sensor are equalized and whereby the transport of water and ions across said flexible diaphragms is reduced.

81. The apparatus of claim 79, wherein said two flexible diaphragms are substantially planar flexible diaphragms.

82. The apparatus of claim 79, wherein said two flexible diaphragms are convoluted to achieve flexibility.

83. An in vivo differential pressure sensor adapted for implantation beneath the skin in the living body and for in vivo calibration after implantation, said sensor comprising:

a. a housing having means defining an opening therethrough;

b. a first flexible diaphragm having an interior side and an exterior side, said first flexible diaphragm extending across the housing opening at one end thereof and being secured to said housing, at least a portion of said exterior side of said first flexible diaphragm defining a portion of the exterior surface of said sensor and being positioned so that after said sensor is implanted beneath the skin said portion of said exterior side of said first flexible diaphragm is in mechanical pressure communication with the skin, whereby pressures external to the living body can be communicated mechanically across the intact skin to said first flexible diaphragm;

c. a second flexible diaphragm having an interior side and an exterior side, said second flexible diaphragm extending across said housing opening at the other end thereof and being secured to said housing, said first and second flexible diaphragm interior sides together with said housing opening defining a chamber within said sensor and, when said sensor is implanted in a living body, said exterior side of said second flexible diaphragm being positioned to be in contact with and in mechanical pressure communication with a bodily medium, the pressure of which is to be sensed;

d. a rigid piston located within said chamber, the rigid piston extending between and being secured to the interior sides of said flexible diaphragms, so that changes in said pressures on said exterior sides of said flexible diaphragms will cause a motion of said flexible diaphragms and said rigid piston, said piston including an electrically conductive portion;

e. parallel resonant circuit means comprising an inductor and a capacitor that are mounted within said housing so that the inductance of said inductor and thus the resonant frequency of said parallel resonant circuit means is varied in accordance with the position of the electrically conductive portion of said rigid piston relative to the inductor, the resonant frequency of said parallel resonant circuit means being detectable by detection apparatus located external to the living body, whereby said resonant frequency changes in accordance with changes in said pressures on said exterior sides of said flexible diaphragms; and, f. a mechanical stop for said piston against said housing when the pressures on said exterior sides of said flexible diaphragms are equal; whereby, when said sensor is implanted beneath the skin, said rigid piston can be driven to said mechanical stop by a pressure external to the living body applied to the skin adjacent to said sensor, and said resonant frequency can be detected at the position of said rigid piston at said mechanical stop after said sensor has been implanted in the living body, and whereby the value of the external pressure applied to the skin required to drive said rigid piston to said mechanical stop, as indicated by said resonant frequency, is equal to the pressure in said bodily medium.

84. The apparatus of claim 83, wherein the inner space of said chamber within said sensor that is not occupied by said rigid piston is filled with an ionic water solution which has similar osmotic pressure as bodily fluids, whereby the difference in the osmotic pressures inside and outside of sensor are equalized and whereby the tranport of water and ions across said flexible diaphragms is reduced.

85. The apparatus of claim 83, wherein said two flexible diaphragms are substantially planar flexible diaphragms.

86. The apparatus of claim 83, wherein said two flexible diaphragms are convoluted to achieve flexibility.

87. An in vivo differential pressure sensor adapted for implantation beneath the skin in the living body and for in vivo calibration after implantation, said sensor comprising:

a. a housing having means defining an opening therethrough;

b. a first flexible diaphragm having an interior side and an exterior side, said first flexible diaphragm means extending across said opening at one end thereof and being secured to said housing, at least a portion of said exterior side of said first flexible diaphragm defining a portion of the exterior surface of said sensor and being positioned so that after said sensor is implanted beneath the skin said portion of said exterior side of said first flexible diaphragm is in mechanical pressure communication with the skin, whereby pressures external to the body can be communicated mechanically across the intact skin to said first flexible diaphragm;

c. a second flexible diaphragm having an interior side and an exterior side, said second flexible diaphragm extending across said opening and being secured to said housing, said first and second flexible diaphragms interior sides and a portion of said housing defining a chamber within said sensor, and said sensor being so adapted that, when said sensor is implanted in a living body, said exterior side of said second flexible diaphragm can be placed in mechanical pressure communication with a bodily medium, the pressure of which is to be sensed;

d. rigid means located within said chamber and secured to both of said flexible diaphragms for coupling the motion of one of said flexible diaphragms to the other of said flexible diaphragms, the motion of said flexible diaphragms being in response to changes in the difference in said pressures on said exterior sides of said flexible diaphragms;

e. contact means connected to said housing for contacting (i) at least one of said diaphragms or (ii) said rigid coupling means thereby defining a mechanical contact reference position within said sensor and with respect to said housing of (i) at least one of said flexible diaphragms or (ii) said rigid coupling means, said mechanical contact reference position corresponding to a predetermined pressure relationship between said pressures on said exterior sides of said flexible diaphragms; and, f. means having a preselected, detectable parameter that is detectable by detection means located outside the living body, said means having a preselected, detectable parameter being at least in part cooperatively connected to and movable with at least one of said flexible diaphragms or said rigid means so that said preselected, detectable, parameter will change with movement of (i) at least a portion of one of said flexible diaphragms or (ii) said rigid coupling means and the value of said preselected, detectable parameter can be detected at said mechanical contact reference position, said at least one flexible diaphragms or said rigid coupling means and said means having a preselected, detectable parameter being so constructed and cooperatively connected that the value of said preselected, detectable parameter changes upon a change from said predetermined pressure relationship; whereby, when said sensor is implanted beneath the skin, said sensor can be driven to said mechanical contact reference position by a pressure external to the living body applied to the skin adjacent to said sensor, and said preselected, detectable parameter can be determined at said mechanical contact reference position after implantation, and whereby the magnitude of the external pressure applied to the skin that is required to drive said sensor to said mechanical contact reference position is a function of the pressure in said bodily medium.

88. The apparatus of claim 87 wherein said mechanical contact reference position means comprises a mechanical stop for at least one of said flexible diaphragms or for said rigid motion coupling means with respect to said housing.

89. The apparatus of claim 87 wherein said mechanical contact reference position means includes electrode contacts that touch at a reference position relative to said housing of (i) at least one of said flexible diaphragms or (ii) said rigid motion coupling means and said means having a preselected, detectable parameter includes circuit means within said sensor cooperative with said electrode contacts whereby the touching of said electrode contacts produces a detectable characteristic response of said circuit means.

90. The apparatus of claim 87 wherein said first and second flexible diaphragms are fluid pressure sealed with respect to said housing.

91. The apparatus of claim 87 wherein said rigid motion coupling means comprise a rigid piston located within said chamber and connected between said flexible diaphragms.

92. The apparatus of claim 87 wherein said mechanical reference position corresponds to the balance of said pressures on said exterior sides of said flexible diaphragms.

93. The apparatus of claim 87 wherein said first and second flexible diaphragms have substantially equal areas and said rigid mechanical coupling has substantially symmetrical diaphragm-contacting ends to provide end-for-end pressure symmetry of said sensor.

94. The apparatus of claim 87 wherein one end of said housing opening is planar, and said first flexible diaphragm is secured to said planar end and is substantially coplanar with said planar opening end at said predetermined pressure relationship of the pressures on said external sides of said flexible diaphragms.

95. The apparatus of claim 87 wherein said means having a preselected, detectable parameter comprises electronic circuit means, said detectable parameter being a characteristic response parameter of said electronic circuit means that is detectable by electromagnetic coupling to an electronic detection means located external to said living body.

96. The apparatus of claim 95 wherein said electronic circuit means includes an inductor and further comprises a magnetic material which moves relative to the inductor with (i) at least one of said flexible diaphragms or (ii) said rigid motion coupling means, such movement producing a displacement of said magnetic material relative to the said inductor, thereby varying the inductance of said inductor, and thus varying said circuit characteristic response parameter.

97. The apparatus of claim 95 wherein said electronic circuit means includes an inductor and further comprises a conductive material which moves relative to the inductor with (i) at least one of said flexible diaphragms or (ii) said rigid motion coupling means, such movement producing a displacement of said conductive material relative to the said inductor, thereby varying the inductance of said inductor, and thus varying said circuit characteristic response parameter.

98. The apparatus of claim 95 wherein said electronic circuit means comprises a resonant electrical circuit which includes a coil and a capacitor, an element of said resonant circuit moving relative to another element of said resonant circuit upon movement of said flexible diaphragms so as to produce a change in said characteristic response parameter.

99. The apparatus of claim 98 wherein said coil is fixed with respect to said housing.

100. The apparatus of claim 95 wherein an element of said resonant circuit moves with said flexible diaphragm so as to vary the capacitance of said capacitor in response to the displacement of (i) at least one of said flexible diaphragm means or (ii) said rigid motion coupling means, thereby varying said characteristic response parameter.

101. The apparatus of claim 98 wherein said resonant electrical circuit is a parallel resonant circuit and wherein said preselected detectable parameter is the resonant frequency of said parallel resonant circuit.

102. The apparatus of claim 87 further comprising means for providing fluid communication between the exterior side of said second flexible diaphragm and an internal bodily fluid, the pressure of which is to be sensed.

103. The apparatus of claim 102 and further comprising a second fluid communication means to allow exit of said internal bodily fluid away from the exterior side of said second flexible diaphragm, whereby said sensor is adapted to be in series connection with a conduit of said internal bodily fluid.

104. The apparatus of claim 103 further comprising fluid shunt valve means interposed in series with at least one of said fluid communication means for regulating the flow of said internal bodily fluid.

105. The apparatus of claim 87 wherein said preselected, detectable parameter varies as a known function of the displacement with respect to said housing (i) at least one of said flexible diaphragms or (ii) said rigid motion coupling means, said displacement being a known function of the difference of said pressures on said exterior sides of said flexible diaphragms.

106. The sensor of claim 87 wherein said means having a preselected, detectable parameter include at least one of said flexible diaphragms.

107. The sensor of claim 87 wherein said means having a preselected, detectable parameter comprises a scatterer of ultrasonic radiation which moves with said flexible diaphragms so that said motion can be detected by ultrasonic radiation source and detection apparatus located outside the living body.

108. The apparatus of claim 87, wherein the inner space of said chamber within said sensor that is not occupied by said rigid means is filled with an ionic water solution which has similar osmotic pressure as bodily fluids, whereby the difference in the osmotic pressures inside and outside of said sensor are equalized and whereby the tranport of water and ions across said flexible diaphragms is reduced.

109. The apparatus of claim 87, wherein said two flexible diaphragms are substantially planar flexible diaphragms.

110. The apparatus of claim 87, wherein said two flexible diaphragms are convoluted to achieve flexibility.

* * * * *